United States Patent [19]

Tsuboi et al.

[11] Patent Number: 4,780,457
[45] Date of Patent: Oct. 25, 1988

[54] INSECTICIDAL COMPOSITION FOR AGRICULTURAL AND HORTICULTURAL USE

[75] Inventors: Shinichi Tsuboi; Shoko Sasaki; Yumi Hattori, all of Tokyo, Japan

[73] Assignee: Nihon Tokushi Noyaku Seizo K.K., Tokyo, Japan

[21] Appl. No.: 79,865

[22] Filed: Jul. 30, 1987

Related U.S. Application Data

[62] Division of Ser. No. 904,087, Sep. 4, 1986, Pat. No. 4,725,589.

[30] Foreign Application Priority Data

Sep. 5, 1985 [JP] Japan ................. 60-194919
Sep. 5, 1985 [JP] Japan ................. 60-194920
Sep. 5, 1985 [JP] Japan ................. 60-194921
Sep. 6, 1985 [JP] Japan ................. 60-195980

[51] Int. Cl.$^4$ ............ A01N 43/40; A01N 43/54; A01N 57/00
[52] U.S. Cl. ..................... 514/89; 514/256; 514/341
[58] Field of Search ............ 514/89, 256, 341

[56] References Cited

U.S. PATENT DOCUMENTS 3,244,586  4/1966  Rigterink ............... 514/89
4,423,028 12/1983  Walker et al. ........... 514/128

OTHER PUBLICATIONS

Australian Patent Abst. AU-A-41097/85 (4/12/85).

Primary Examiner—Allen J. Robinson
Attorney, Agent, or Firm—Sprung Horn Kramer & Woods

[57] ABSTRACT

A synergistic insecticidal composition comprising a nitromethylene derivative of the formula

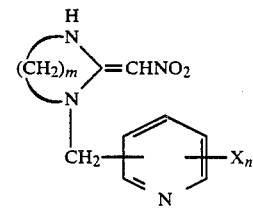

in which
 X is a lower alkyl group, a lower alkoxy group or a halogen atom,
 n is 0, 1 or 2, and
 m is 2 or 3, and
an insecticide which is a carboxylic acid ester, carbamate, organophosphate ester or one of a group of specific compounds.

3 Claims, No Drawings

INSECTICIDAL COMPOSITION FOR AGRICULTURAL AND HORTICULTURAL USE

This is a division of application Ser. No. 904,087, filed Sept. 4, 1986, now U.S. Pat. No. 4,725,589.

The present invention relates to novel insecticidal synergistic active substance combinations of known nitromethylene derivatives and known insecticides.

Nitromehylene derivatives and their use as insecticides have already been disclosed in Japanese patent application Nos. 20620/1984, 72966/1984 and 132943/1984.

It has already been disclosed that the following insecticides have insecticidal activity: S,S'-2-dimethylaminotrimethylene bis(thiocarbamate), N,N-dimethyl-1,2,3-trithian-4-ylamine, 2-tert-butylimino-3-isopropyl-5-phenyl-1,3,5-thiadiazinan-4-one and 1-(4-chlorophenyl)-3-(2,6-difluorobenzoyl)urea (The Pesticide Manual, 7th edition, 1983 published by the British Crop Protection Council), N-(2,6-di-fluorobenzoyl)-N'-[3,5-dichloro-4-(3-chloro-5-trifluoromethyl-2-pyridyloxy)phenyl]urea (Japanese patent publication No. 53786/1982), and 3-phenoxy benzyl 2-(4-ethoxyphenyl)-2-methylpropylether (Japanese laid open patent application No. 72928/1982).

However, the activities of these known insecticidal compounds are not entirely satisfactory especially when the concentrations of these active compounds are low and when they are used only in small amounts.

It was furthermore already been disclosed that the following carboxylic acid esters have insecticidal activity: for example, α-cyano-5-phenoxy-4-fluoro-benzyl 3-(2,2-dichlorovinyl)-2,2-dimethylcyclopropanecarboxylate (Japanese patent publication No. 57025/1982), (RS)-α-cyano-3-phenoxybenzyl (Z)-(1RS,3RS)-(2-chloro-3,3,3-trifluoropropenyl)-2,2-dimethylcyclopropanecarboxylate, (RS)-α-cyano-3-phenoxy-benzyl-2,2,3,3-tetramethylcyclopropanecarboxylate, (RS)-α-cyano-3-phenoxybenzyl (RS)-2-(4-chlorophenyl)-3-methylbutyrate, and α-cyano-3-phenoxybenzyl 1-p-ethoxyphenyl-2,2-dichlorocyclopropane-1-carboxylate (see the Pesticide Manual, 7th Edition, 1983, published by the British Crop Protection Council).

However, the activities of these known insecticidal compounds are not entirely satisfactory when their concentrations as active compounds are low or when they are applied only in small amounts.

It has furthermore already been disclosed that the following carbamates have insecticidal activity, for example, 2-isopropoxyphenyl methylcarbamate, 2-sec-butylphenyl methylcarbamate, m-tolyl methylcarbamate, 3,4-xylyl methylcarbamate, 2,3-dihydro-2,2-dimethylbenzofuran-7-yl methylcarbamate, α-ethylthio-o-tolyl methylcarbamate, and 2-dimethylamino-5,6-dimethylcarbamate [see The Pesticide Manual, 7th edition, 1983 (published by the British Crop Protection Council].

However, the activity of these known carbamates is not necessarily satisfactory when their concentration is low or they are applied only in small amounts. Moreover, as a result of using these insecticides over several yeas, some insects have gained resistance to some of these insecticides and these insects have become very difficult to control.

It has furthermore been disclosed that the following organophosphate esters have insecticidal activity: for example, O-ethyl O-4-methylthiophenyl S-propyl phosphorodithioate,
O-2,4-dichlorophenyl O-ethyl S-propyl phosphorodiothioate,
O,O-diethyl O-5-phenylisoxazol-3-yl phosphorothioate,
2,3-dihydro-3-oxo-2-phenyl-6-pyridazinyl diethyl phosphorothioate,
O,S-dimethyl acetylphosphoramidothioate,
O,O-diethyl S-2-ethylthioethyl phosphorodithioate, and
O,O-dimethyl S-2-(1-methylcarbamoylethylthio) ethyl phosphorothioate (see The Pesticidal Manual, 7th Edition, 1983, published by the British Crop Protection Council).

However, the activity of these known organo-phosphates is not necessarily satisfactory when their concentrations are low or they are applied only in small amounts. Furthermore, as a result of using these insecticides over several years, some pests have acquired resistance to some of these chemicals, and it has become extremely difficult to control these pests.

It has been found that novel active substance combinations of (1) a nitromethylene derivative represented by the formula (I)

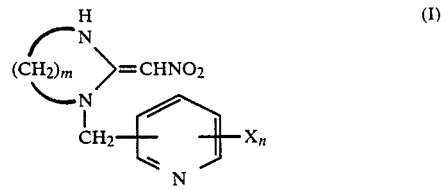

wherein X represents a lower alkyl group, a lower alkoxy group or a halogen atom, n represents 0, 1 or 2, and m represents 2 or 3, and at least one insecticidal compound selected from one of the following groups (2) to (5):

(2) group of insecticides consisting of S,S'-2-dimethylaminotrimethylene bis(thiocarbamate), N,N-dimethyl-1,2,3-trithian-5-ylamine, 2-tert-butylimino-3-isopropyl-5-phenyl-1,3,5-thiadiazinan-4-one, 1-(4-chlorophenyl)-3-(2,6-difluorobenzoyl)urea, N-(2,6-difluorobenzoyl)-N'[3,5-dichloro-4-(3-chloro-5-trifluoromethyl-2-pyridyloxy)-phenyl]urea, 3-phenoxybenzyl 2-(4-ethoxyphenyl)-2-methylpropylether, 1-(4-trifluoromethoxy-phenyl)-3-(2-chlorobenzoyl)urea, 1-(4-(2-dichloro-1-difluoro-ethoxy)phenyl-3-(2-chlorobenzoyl)urea, 1-(4-trifluorophenyl)-3-(2,6-difluorobenzoyl)urea, 1-(2,4-difluoro-3,5-dichlorophenyl)-3-(2,6-difluorobenzoyl)urea, and N-[6-(2,2,3-trifluoro-3-chloro-benzodioxin-(1,4))]-N'-(2,6-difluorobenzoyl)urea, (3) group of carboxylic acid esters of the following formula

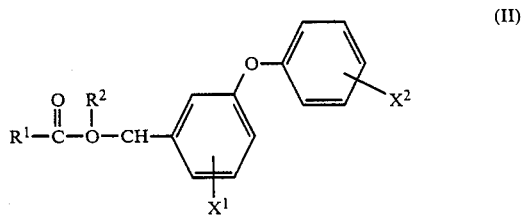

wherein $R^1$ represents a substituted lower alkyl group or a substituted cyclopropyl group, $R^2$ represents a hydrogen atom or CN, and each of $X^1$ and $X^2$ represents a hydrogen or halogen atom, (4) group of carbamates of the following formula

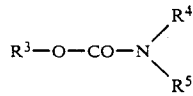  (III)

wherein $R^3$ represents a substituted or unsubstituted aryl group, heterocyclic group or oxime group, $R^4$ represents a hydrogen atom or a lower alkyl group, and $R^5$ represents a lower alkyl group or the group

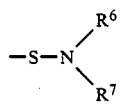

in which $R^6$ represents a lower alkyl group, and $R^7$ represents a lower alkyl group, a lower alkoxycarbonyl group or a lower alkoxycarbonyl alkyl group, (5) group of organophosphate esters of the following formula

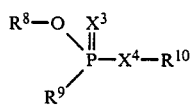  (IV)

wherein $X^3$ represents an oxygen or sulfur atom, $X^4$ represents an oxygen or sulfur atom, or a direct bond between the phosphorus atom and $R^{10}$ in the formula, $R^8$ represents a lower alkyl group, $R^9$ represents a lower alkoxy group, a lower alkylthio groups, a lower alkylcarbonylamide group or a phenyl group, and $R^{10}$ represents a substituted or unsubstituted lower alkyl, lower alkenyl, phenyl or heteroaryl group, or $R^9$ and $R^{10}$ together represent a phosphorine ring together with the phosphorus atom and $X^4$ in the formula, exhibit a particular high insecticidal activity.

Surprisingly, the insecticidal activity of the active substance combinations according to the invention is substantially greater than the sum of the effects of the individual active substances. Accordingly, a genuine synergistic effect is present.

By applying the active substance combinations according to the invention, one can achieve a cooperative and synergistic effect against paddy pests such as hemipterous plant hoppers (e.g., white-backed planthopper) and lepidopterous paddy leaf roller and pests on horticultural crops including fruits and vegetables, such as lepidopterous diamondback moths in lower concentrations than the active compound applied individually, and furthermore a residual effect, can be detected.

The insecticidal composition of this invention therefore provides a technical advantage which is very effective in the cultivation of agricultural and horticultural crops and is of outstanding industrial utility and applicability.

The nitromethylene derivatives of general formula (I) used in the active substance combinations according to the invention are defined by the following formula

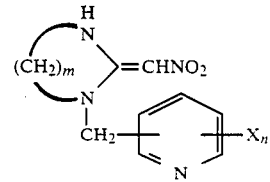  (I)

wherein X represents a lower alkyl group, a lower alkoxy group, or a halogen atom, n represents 0, 1 or 2 and m represents 2 or 3.

In formula (I), preferably, X represents a methyl group, a methoxy group, a chlorine atom, a bromine atom or a fluorine atom, p represents 1 or 2, m represents 2 or 3, and the bonding position on the pyridine ring is 3- (or 5-).

The nitromethylene derivatives of general formula (I) can exist also in the form of salts. Examples of the salts include inorganic acid salts, sulfonic acid salts, organic acid salts and metal salts, preferably hydrochlorides, p-toluenesulfonates, cupric acetates, and succinates. Accordingly, the nitromethylene derivatives of formula (I), as used herein, denote their salts as well.

Examples of the nitromethylene derivatives of the formula (I) used in the active substance combination according to the invention include 1-(3-pyridylmethyl)-2-(nitromethylene)tetrahydropyrimidine, 1-(2-methyl-5-pyridylmethyl)-2-(nitromethylene)imidazolidine, 1-(2-methyl-5-pyridylmethyl)-2-(nitromethylene)tetrahydropyrimidine, 1-(2-methoxy-5-pyridylmethyl)-2-(nitromethylene)imidazolidine, 1-(2-methoxy-5-pyridylmethyl)-2-(nitromethylene)tetrahydropyrimdine, 1-(2-chloro-5-pyridylmethyl)-2-(nitromethylene)imidazolidine, 1-(2-chloro-5-pyridylmethyl)-2-(nitromethylene)tetrahydropyrimidine, 1-(2-fluoro-5-pyridylmethyl)-2-(nitromethylene)imidazolidine, 1-(2-fluoro-5-pyridylmethyl)-2-(nitromethylene)tetrahydropyrimdine, 1-(2-bromo-5-pyridylmethyl)-2-(nitromethylene)imidazolidine, 1-(2-bromo-5-pyridylmethyl)-2-(nitromethylene)tetrahydropyrimidine, 1-(5-chloro-2-pyridylmethyl)-2-(nitromethylene)imidazolidine, 1-(5-chloro-2-pyridylmethyl)-2-(nitromethylene)tetrahydropyrimidine, 1-(2,4-dichloro-5-pyridylmethyl)-2-(nitromethylene)tetrahydropyrimidine, 1-(2,4-dibromo-5-pyridylmethyl)-2-(nitromethylene)imidazolidine, 1-(2,3-dichloro-5-pyridylmethyl)-2-(nitromethylene)imidazolidine, 1-(3-pyridylmethyl)-2-(nitromethylene)tetrahydropyrimidine hydrochloride, 1-(2-methyl-5-pyridylmethyl)-2-(nitromethylene)tetrahydropyrimidine p-toluenesulfonate, 1-(2-methoxy-5-pyridylmethyl)-2-(nitromethylene)tetrahydropyrimdine succinate, 1-(2-chloro-5-pyridylmethyl)-2-(nitromethylene)imidazolidine hydrochloride, 1-(2-fluoro-5-pyridylmethyl)-2-(nitromethylene)tetrahydropyrimidine cupric acetate,
1-(2-bromo-5-pyridylmethyl)-2-(nitromethylene)imidazolidine succinate, and
1-(2,4-dichloro-5-pyridylmethyl)-2-(nitromethylene)tetrahydropyrimidine p-toluenesulfonate.

The insecticidal activity of the nitromethylene derivatives of general formula (I) is described in Japanese patent application Nos. 26020/1984, 72966/1984 and 13294371984.

Examples of the known insecticides of the other component selected from group (2) above are as follows:
S,S'-2-dimethylaminotrimethylene bis(thiocarbamate) (cartap),
N,N-dimethyl-1,2,3-trithian-5-ylamine (thiocyclam),
2-(tert-butylimino-3-iso-propyl-5-phenyl-1,3,5-thiadiazinan-4-one (buprofezin), 1-(4-chlorophenyl)-3-(2,6-difluorobenzoyl)urea (difluorozuron) (The Pesticide Manual, 7th edition, 1983 published by the British Crop Protection Council).
N-(2,6-difluorobenzoyl)-N'-[3,5-dichloro-4-(3-chloro-5-trifluoromethyl-2-pyridyloxy)phenyl]urea (Japanese Patent Publication No. 53786(1982), and 3-phenoxybenzyl 2-(4-ethoxyphenyl)-2-methyl-propylether (Japanese Laid Open Application No. 72928/1982).

Preferred carboxylic acid esters (group (3)) of the formula (II) used in the active substance combinations according to the invention are those of the general formula (II) in which $R^1$ represents an alkyl group substituted by a phenyl group which is substituted by a substituent selected from halogen atoms, lower alkoxy groups and lower haloalkoxy groups, and the alkyl group may further be substituted by a dichlorocyclopropane group, or $R^1$ represents an alkyl group substituted by a phenylamino group which is substituted by a halogen atom and/or haloalkyl group, the preferred haloalkyl group being a trifluoromethyl group, or $R^1$ represents a cyclopropyl group substituted by an alkyl group having 1 to 3 carbon atoms, preferably a methyl group, or a cyclopropyl group substituted by an alkyl group having 1 to 3 carbon atoms, preferably a methyl group, and a halogenoalkenyl group having 2 to 3 carbon atoms;

$R^2$ represents a hydrogen atom or CN; and each of $X^1$ and $X^2$ represents a hydrogen atom, a chlorine atom or a fluorine atom, preferably $X^1$ represents a hydrogen or fluorine atom, and $X^2$ represents a hydrogen atom.

Examples of the carboxylic acid esters of general formula (II) include
α-cyano-5-phenoxy-4-fluoro-benzyl(3-(2,2-dichlorovinyl)-2,2-dimethylcyclopropanecarboxylate (cyfluthrin),
3-phenoxybenzyl(1RS,3RS;1RS,3RS)-3-(2,2-dichlorovinyl)-2,2-dimethylcyclopropanecarboxylate (permethrin,
(RS)-α-cyano-3-phenoxybenzyl(1RS,3RS;1RS,3SR)-3-(2,2-dichlorovinyl)-2,2-dimethylcyclopropanecarboxylate (cypermethrin),
(S)-α-cyano-3-phenoxybenzyl(1R,3R)-3-(2,2-dibromovinyl)-2,2-dimethylcyclopropanecarboxylate (deltamethrin),
(RS)-α-cyano-3-phenoxybenzyl(Z)-(1RS,3RS)-(-2-chloro-3,3,3-trifluoropropenyl)-2,2-dimethylcyclopropanecarboxylate (cyhalothrin),
(RS)-α-cyano-3-phenoxybenzyl 2,2,3,3-tetramethylcyclopropanecarboxylate (fenpropathrin),
(RS)-α-cyano-3-phenoxybenzyl(RS)-2-(4-chlorophenyl)-3-methylbutyrate (fenvalerate),
(RS)-α-cyano-3-phenoxybenzyl(S)-2-(4-difluoromethoxyphenyl)-3-methylbutyrate (flucythrinate),
α-cyano-3-phenoxybenzyl 1-p-ethoxyphenyl-2,2-dichlorocyclopropan-1-carboxylate, and
(RS)-α-cyano-3-phenoxybenzyl N-(2-chloro-α,α,α-trifluoro-p-tolyl)-D-valinate (fluvalinate).

The carboxylic acid esters as one component of the active substance combinations according to the invention have already been known. For example, they are described as insecticides in The Pesticide Manual, 7th Edition, 1983, published by The British Crop Protection Council.

Preferred carbamates (group (4)) are those of general formula (III) in which $R^3$ represents a phenyl group substituted by one or two same or different alkyl groups, alkoxy groups having 1 to 4 carbon atoms or ethylthiomethyl groups; or $R^3$ represents a naphthyl group, a pyrimidinyl group substituted by a dialkylamino group having 1 to 3 carbon atoms, preferably a dimethylamino group and two alkyl groups having 1 to 4 carbon atoms, preferably methyl groups, or a 2,3-dihydrobenzofuranyl or benzoxazolyl group substituted by an alkyl group having 1 to 4 carbon atoms, preferably a methyl group; or $R^3$ represents a group of the general formula

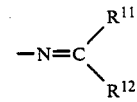

in which $R^{11}$ represents an alkyl group having 1 to 4 carbon atoms, preferably a methyl group, and $R^{12}$ represents an alkylthio group having 1 to 4 carbon atoms, preferably a methylthio group; $R^4$ represents a hydrogen atom or an alkyl group having 1 to 4 carbon atoms, preferred alkyl group having 1 to 4 carbon atoms of $R^4$ represents a methyl group; and $R^5$ represents an alkyl group having 1 to 4 carbon atoms, preferably a methyl group, or a group of the formula

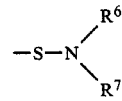

in which $R^6$ represents an alkyl group having 1 to 5 carbon atoms, and $R^7$ represents an alkyl group, an alkoxycarbonyl group or an alkoxycarbonylalkyl group, each having 1 to 5 carbon atoms.

Examples of the carbamates of general formula (III) include
2-isopropoxyphenyl methylcarbamate (propoxur),
o-cumenyl methylcarbamate (isoprocarb),
2-sec-butylphenyl methylcarbamate (BPMC),
3,4-xylyl methylcarbamate (xylylcarb),
m-tolyl methylcarbamate (metolcarb),
3,5-xylyl methylcarbamate (XMC),
α-ethylthio-o-tolyl methylcarbamate (ethiofencarb),
1-naphthyl methylcarbamate (carbaryl),
2-dimethylamino-5,6-dimethylpyrimidin-4-yl dimethylcarbamate (pirimicarb),
2,2-dimethyl-1,3-benzodioxol-4-yl methylcarbamate (bendiocarb), 2,3-dihydro-2,2-dimethylbenzofuran-7-yl methylcarbamate (carbofuran),
butyl 2,3-dihydro-2,2-dimethylbenzofuran-7-yl N,N-dimethyl-N,N-thiodicarbamate (furanthiocarb),
2,3-dihydro-2,2-dimethylbenzofuran-7-yl(dibutyl)aminosulfenyl)(methyl)carbamate (carbosulfan) (See Japanese patent publication No. 39487/1983),
2,3-dihydro-2,2-dimethylbenzofuran-7-yl N-(N-isopropyl-N-ethoxycarbonylethylaminosulfenyl)-N-methylcarbamate (aminosulfulan) (See Japanese patent laid open application No. 200377/1982), and
S-methyl N-(methylcarbamoyloxy)thioacetimidate (methomyl).

The carbamates used as one component of the active substance combinations according to the invention are already known. For example, they are described in The Pesticide Manual, 7th edition, 1983 (published by The British Crop Protection Council).

Preferred organophosphate esters (group (5)) are those of the general formula (IV) in which
$R^8$ represents an alkyl group having 1 to 4 carbon atoms,
$R^9$ represents an alkoxy group, an alkylthio group, an alkylcarbonylamide group, each having 1 to 4 carbon atoms, or a phenyl group,
$R^{10}$ represents a phenyl group substituted by one or two substituents selected from halogen atoms and methyl, methylthio, nitro and cyano groups, or
$R^{10}$ represents an alkyl group having 1 to 3 carbon atom which may optionally be substituted by a halogen atom, an alkylthio (or sulfinyl) group having 2 to 3 carbon atoms, a phenyl group, an alkoxycarbonyl group having 1 to 4 carbon atoms, an alkylcarbamoyl group having 1 to 4 carbon atoms, an alkylcarbamoylalkyl($C_{1-2}$)thioalkyl $C_{(1-2)}$ group or an alkoxycarbonyl-N-methylcarbamoyl group having 1 to 4 carbon atoms, a halogen-substituted benzoxazole group, or an alkyl group having 1 to 2 carbon atoms substituted by a halogen atom and a phthalimide group, or
$R^{10}$ represents an alkenyl group having 2 to 3 carbon atoms substituted by one or two substituents selected from halogen atoms, halogen sustituted phenyl group and alkylcarbamoyl group, or
$R^{10}$ represents a pyridinyl, pyrimidinyl, pyridazinyl, quinoxalinyl, isoxazolyl or oxo-1,3,4-thiadiazolyl group substituted by 1 to 3 same or different alkyl groups, alkoxy groups, dialkylamino groups, each having 1 to 4 carbon atoms, halogen atoms, or phenyl groups, or
$R^9$ and $R^{10}$ together represent a benzodioxaphosphorine ring, or
when $X_4$ represents a direct bond between the phosphorus atom and $R^{10}$, $R^{10}$ represents the group

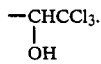

Examples of the organophosphates of general formula (IV) are
O,O-dimethyl O-4-methylthio-m-tolyl phosphorothioate (fenthion),
O,O-dimethyl O-4-nitro-m-tolyl phosphorothioate (fenitrothion),
4-(methylthio)phenyl dipropyl phosphate (propaphos),
O-4-cyanophenyl O,O-dimethyl phosphorothioate (cyanophos),
O,2,4-dichlorophenyl O-ethyl S-propyl phosphorodithioate (prothiofos),
O-ethyl O-4-methylthiophenyl S-propyl phosphorodithioate (sulprofos),
O-4-bromo-2-chlorphenyl O-ethyl S-propyl phosphorothioate (profenofos),
O-ethyl O-4-nitrophenyl phenylphosphonothioate (EPN),
O-4-cyanophenyl O-ethyl phenylphosphonothioate (cyanofenphos),
O,S-dimethyl acetylphosphoramidothioate (acephate),
S-2-ethylsulfinyl-1-methylethyl O,O-dimethyl phosphorothioate (oxydeprofos),
O,O-diethyl S-2-ethylthioethyl phosphorodithioate (disulfoton),
S-2-ethylthioethyl O,O-dimethyl phosphorodithioate (thiometon),
S-α-ethoxycarbonylbenzyl O,O-dimethyl phosphorodithioate (phenthoate),
S-1,2-bis(ethoxycarbonyl)ethyl O,O-dimethyl phosphorodithioate (malathion),
O,O-dimethyl S-methylcarbamoylmethyl phosphorodithioate (dimethoate),
O,O-dimethyl S-S-(1-methylcarbamoylethylthio)ethyl phosphorothioate (vamidothion),
S-(N-ethoxycarbonyl-N-methylcarbamoylmethyl) O,O-diethyl phosphorodithioate (mecarbam),
dimethyl 2,2,2-trichloro-1-hydroxyethylphosphonate (trichlorphon),
1,2-dibromo-2,2-dichloroethyl dimethyl phosphate (naled),
2,2-dichlorovinyl dimethyl phosphate (dichlorvos),
2-chloro-1-(2,4-dichlorophenyl)vinyl diethyl phosphate (chlorofenvinphos),
(Z)-2-chloro-1-(2,4,5-trichlorophenyl)vinyl dimethyl phosphate (tetrachlorvinphos),
dimethyl (E)-1-methyl-2-(methylcarbamoyl)vinyl phosphate (monocrotophos),
S-6-chloro-2,3-dihydro-2-oxobenzoxazol-3-ylmethyl O,O-diethyl phosphorodithioate (phosalone),
S-2-chloro-1-phthalimidoethyl O,O-diethyl phosphorodithioate (dialifos),
O,O-dimethyl O-3,5,6-trichloro-2-pyridyl phosphorothioate (chlorpyrifos-methyl),
O,O-diethyl O-3,5,6-trichloro-2-pyridyl phosphorothioate (chlorpyrifos),
O-2-diethylamino-6-methylpyrimidin-4-yl, O,O-dimethyl phosphorothioate (pirimophos-methyl),
O,O-diethyl O-2-isopropyl-6-methylpyrimidin-4-yl phosphorothioate (diazinon),
O-6-ethoxy-2-ethylpyrimidin-4-yl O,O-dimethyl phosphorothioate (etrimfos),
2,3-dihydro-3-oxo-2-phenyl-6-pyridazinyl diethyl phosphorothioate (pyridaphenthion),
O,O-diethyl O-quinoxalin-2-yl phosphorothioate (quinalphos),
O,O-diethyl O-5-phenylisoxazol-3-yl phosphorothioate (isoxathion),
S-2,3-dihydro-5-methoxy-2-oxo-1,3,4-thiaziazol-3-ylmethyl O,O-dimethyl phosphorodithioate (methidathion), and
2-methoxy-4H-1,3,2λ⁵-benzodioxaphosphorine-2-sulfide (salithion).

The organophosphate esters, one component of the active substance combinations according to the invention, are already known, and are described, for example, in The Pesticide Manual, 7th edition, 1983 (published by The British Crop Protection Council) as inseciticides.

Among the above organophosphates, quinalphos, fenthion, sulprofos, phenthoate, fenitrothion, diazinon, isoxathion, pyridaphenthion, trichlorphon, chlorpyrifosmethyl, malathion, monocrotophos, propaphos, EPN, etrimfos and tetrachlorvinphos, for example, are used preferably for the control of lepidoptereous pests in paddies, such as paddy leaf roller (*Cnaphalocrocis medinalis*) and rice stem borer (*Chilo suppressalis*).

Prothiofos, sulprofos, dichlorovos, trichlorphon, cyanophos, pyrimophos-methyl, chloropyrifos, dimethoate, phosalone, methidathion, chlorofenvinphos, acephate, salithion, dialifos, mecarbam, profenofos, naled, phenthoate, fenitrothion, diazinon, isoxathion, malathion, EPN and cyanofenphos, for example, are used preferably for the control of lepidoptereous pests in horticulture such as diamonback moths (*Plutella m culipennis*), cabbage armyworms (*Mamestra brassicae*) and leaf rollers.

Furthermore, disulfoton, vamidothion, thiometon and oxydeprofos, for example, are used preferably for horticulture, especially for controlling hemipterous pests such as aphids including aphids on peach, cotton and apple.

The weight ratios of the groups of active substances in the active substance combinations can vary within relative wide ranges. In general, 0.05 to 10 parts by weight of active substance of the group of active substances (2), preferably 0.1 to 5 parts by weight, are used per part by weight of active substance of the group of active substances (1).

Furthermore in general, 0.05 to 10 parts by weight of active substance of the group of active substance (3) (carboxylic acid esters of formula (II)), preferably 0.1 to 5 parts by weight, are used per part by weight of active substance of the group of active substances (1).

Furthermore in general, 0.1 to 20 parts by weight of active substance of the group of active substances (4) (carbamates of general formula (III)), preferably 0.2 to 15 parts by weight, are used per part by weight of active substance of the group of active substances (1).

Furthermore in general, 0.05 to 10 parts by weight of active substance to the group of active substances (5) (organophosphate esters of formula (IV)), preferably 0.1 to 5 parts by weight, are used per part by weight of active substance of the group of active substances (1).

The active substance combinations according to the invention exhibit an excellent insecticidal activity. Hence, the active substance combinations can be used as an insecticide by foliar application, underwater or water surface application, soil application, soil mixing treatment, application to nursery box, etc.

The active substance combinations according to the invention show strong insecticidal activity and therefore can be used as an insecticide. The active substance combinations according to the invention have no phytotoxicity to cultivated plants and low toxicity to warmblooded animals, and can be used to accurately control pests, particularly insects, in agriculture and forestry, and in protecting stored crops and products. They are active against sensitive and resistant species and against all or some stages of development.

For example, the active substance combinations according to the invention can be effectively used to control paddy pests, for example hemipterous plant hoppers (such as brown planthopper, white-backed planthopper and smaller brown planthopper) and leafhoppers, lepidopterous larvae (rice stem borer, paddy leaf rolle, etc.), and coleopterous rice plant weevil, and pests on horticultural crops such as fruit trees and vegetables, for example lepidopterous larvae (diamondback moth, armyworms, leaf roller, etc.) and hemipterous scales and aphids.

The active substance combinations according to the invention exhibit powerful insecticidal effects. They can therefore be used against the following pests.

| Coleopterous insects |
|---|
| *Callosobruchus chinensis,* |
| *Sitophilus zeamais,* |
| *Tribolium castaneum,* |
| *Epilachna vigintioctomaculata,* |
| *Agriotes fuscicollis,* |
| *Anomala rufocuprea,* |
| *Leptinotarsa decemkineata,* |
| Diabrotica spp., |
| *Monochamus alternatus,* |
| *Lissorhoptrus, oryzophilus,* and |
| *Lyctus bruneus.* |
| Lepidopterous insects |
| *Lymantria dispar,* |
| *Malacosoma neustria,* |
| *Pieris rapae,* |
| *Spodoptera litura,* |
| *Mamestra brassicae,* |
| *Chilo suppressalis,* |
| *Pyrausta nubilalis,* |
| *Ephestia cautella,* |
| *Adoxophyes orana,* |
| *Carpocapsa pomonella,* |
| *Agrotis fucosa,* |
| *Galleria mellonella,* |
| *Plutella maculipennis,* |
| *Heliothis virscens,* and |
| *Phyllocnistis citrella.* |
| Hemipterous insects |
| *Nephotettix cincticeps,* |
| *Nilaparvata lugens,* |
| *Laodelphax striatellus,* |
| *Sogatella furcifera,* |
| *Pseudococcus comstocki,* |
| *Unaspis yanonensis,* |
| *Myzus persicae,* |
| *Aphis pomi,* |
| *Aphis gossypii,* |
| *Ropalosiphum pseudobrassicae,* |
| *Stephanitris nashi,* |
| Nezara spp., |
| *Trialeurodes vaporariorum,* and |
| Psylla spp. |
| Orthopterous insects |
| *Gryllotalpa afticana* and *Locusta migratoria migratoriodes.* |

The active substance combinations can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active substance combinations with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalene, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agent there may be used non-ionic and anionic emulsifiers, such as polyoxyethylene-fatty acid esters, polyoxyethylene-fatty alcohol ethers, for example, alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestufs or metal phthalocyanine dyestuffs, and trace nutrients, such as salts of iron, manganese boron, copper, cobalt, molybdenum and zinc.

The formulations in general in general contain from 0.1 to 95 percent by weight of active compound, preferably from 0.5 to 90 percent by weight.

The active substance combinations according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinates hydrocarbons, phenylureas, and substances produced by microorganisms.

The active substance combinations according to the invention can be furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.00001 to 100% by weight of active compound, preferably between 0.00004 and 1% by weight.

The compounds are employed in a customary manner appropiate for the use forms.

When used against pests of stored products, the active compounds are distinguished by an excellent residual action on wood and clay as well as a good stability to alkali on limed substrates.

The following examples illustrate the present invention more specifically. It should be understood, however, that the invention is in no way limited to these examples alone.

(A) Biological Examples relating to novel active substance combinations of (1) a nitromethylene derivative of formula (I) and an insecticidal compound of group (2);

EXAMPLE 1

Cnaphalocrosis test

Preparation of a test chemical
 Solvent: 3 parts by weight of xylol
 Emulsifier: 1 part by weight of polyoxyethylene alkyl phenyl ether To prepare a formulation of active compounds, 1 part by weight of the active compounds was mixed with the aforesaid amount of the solvent containing the aforesaid amount of the emulsifier, and the mixture was diluted to a predetermined concentration with water.

Testing method

Three rice seedlings, 15 cm tall, were planted in each of vinyl resin pots having a diameter of 9 cm. Ten days after the plantation, a water dilution of the active compounds in a predetermined concentration prepared as above was sprayed onto the plants in an amount of 20 ml per pot by means of a spray gun. After air drying the spray, a plastic net cylinder having a diameter of 9 cm and a height of 25 cm was put over each pot, and ten 4th instar larvae of paddy leaf rollers (*Cnaphalocrosis medinalis* Gueneer) were inoculated in each pot. The pots were each placed in a constant temperature chamber, and two days later, the number of dead insects was counted. The kill ratio was then calculated. The above test was carried out through two replicates.

The results are shown in Table 1.

TABLE 1

| | Cnaphalocrosis test | |
|---|---|---|
| Test chemical | Concentration of the active ingredient (ppm) | Kill ratio (%) |
| No. 1 + [A] | 40 + 8 | 100 |
| No. 1 + [B] | 40 + 8 | 100 |
| No. 2 + [A] | 40 + 8 | 100 |
| No. 2 + [B] | 40 + 8 | 100 |
| No. 3 + [A] | 40 + 8 | 100 |
| No. 3 + [B] | 40 + 8 | 100 |
| No. 4 + [A] | 40 + 8 | 100 |
| No. 4 + [B] | 40 + 8 | 100 |
| No. 5 + [A] | 40 + 8 | 100 |
| No. 5 + [B] | 40 + 8 | 100 |
| No. 1 | 40 | 10 |
| No. 2 | 40 | 15 |
| No. 3 | 40 | 15 |
| No. 4 | 40 | 20 |
| No. 5 | 40 | 30 |
| [A] | 8 | 30 |
| [B] | 8 | 45 |

TABLE 1-continued

| | Cnaphalocrosis test | |
|---|---|---|
| Test chemical | Concentration of the active ingredient (ppm) | Kill ratio (%) |
| Non-treated | — | 0 |

Note
1. None of the mixed and single chemicals used in the tests of this example showed phytotoxicity.
2. Compounds of general formula (I) used in this invention:
Compound No. 1: 1-(2-methyl-5-pyridylmethyl)-2-(nitromethylene)tetrahydropyrimidine.
Compound No. 2: 1-(2-methoxy-5-pyridylmethyl)-2-(nitromethylene)tetrahydropyrimidine.
Compound No. 3: 1-(2-bromo-5-pyridylmethyl)-2-(nitro-methylene)tetrahydropyrimidine.
Compound No. 4: 1-(2-chloro-5-pyridylmethyl)-2-(nitromethylene)imidazolidine.
Compound No. 5: 1-(2-fluoro-5-pyridylmethyl)-2-(nitromethylene)imidazolidine.
3. Compounds (according to group (2) insecticides mentioned above, used in this invention:
[A]: cartap
[B]: thiocyclam

EXAMPLE 2

Sogatella test

Three rice plants, about 15 cm tall, were planted in each of pots having a diameter of about 13 cm, and 10 days after the plantation, a water dilution of the active compounds in a predetermined concentration prepared as in Example 1 was sprayed onto the plants in an amount of 20 ml per pot by means of a spray gun. Ten days and 20 days after the spraying, a cage was put over each pot, and ten 3rd instar larvae of white-backed planthopper (*Sogatella furcifera*) were inoculated in each pot. The pots were each placed in a constant temperature chamber, and 2 days and 7 days later, the number of dead insects was counted. The kill ratio was then calculated. The above test was carried out through two replicates.

The results are shown in Table 2.

TABLE 2

| | Sogatella test | | | | |
|---|---|---|---|---|---|
| | | Kill ratio (%) | | | |
| | Concentration of the active | Inoculated 10 days later | | Inoculated 20 days later | |
| Test chemical | ingredient (ppm) | 2 days later | 7 days later | 2 days later | 7 days later |
| No. 1 + [A] | 8 + 8 | 100 | — | 90 | 100 |
| | 4 + 4 | 65 | 100 | 20 | 80 |
| No. 2 + [A] | 8 + 8 | 100 | — | 90 | 100 |
| | 4 + 4 | 45 | 100 | 30 | 80 |
| No. 3 + [A] | 8 + 8 | 100 | — | 100 | — |
| | 4 + 4 | 80 | 100 | 40 | 100 |
| No. 4 + [A] | 8 + 8 | 100 | — | 100 | — |
| | 4 + 4 | 90 | 100 | 40 | 100 |
| No. 5 + [A] | 8 + 8 | 100 | — | 100 | — |
| | 4 + 4 | 100 | — | 75 | 100 |
| No. 1 | 8 | 30 | 40 | 10 | 10 |
| No. 2 | 8 | 40 | 45 | 15 | 20 |
| No. 3 | 8 | 80 | 80 | 30 | 30 |
| No. 4 | 8 | 75 | 80 | 35 | 40 |
| No. 5 | 8 | 90 | 90 | 35 | 35 |
| [A] | 8 | 0 | 85 | 0 | 70 |
| Non-treated | — | 0 | 0 | 0 | 0 |

Note
1. None of the mixed and single chemicals used in Example 2 showed phytotoxicity.
2. Compounds Nos. 1, 2, 3, 4 and 5 of general formula (I) used in this invention are the same as those given in Example 1.
3. Compound (according to group (2) insecticides mentioned above) used in this invention.
[A]: buprofezin

EXAMPLE 3

Plutella test

Testing method

A water dilution of the active compounds in a predetermined concentration prepared as in example 1 was sprayed onto cabbage seedlings before head formation, about 15 cm tall, planted in pots having a diameter of cm in an amount of 20 ml per pot by means of spray gun. The spray was air-dried, and ten 2nd instar larvae of diamondback moth (*Plutella maculipennis*) were inoculated in each pot. The pots were placed in a constant temperature chamber, and the number of dead insects was counted 2 days and 7 days later. The kill ratio was calculted. The test was carried out through two replicates.

The results are shown in Table 3.

TABLE 3

| | Plutella test | | |
|---|---|---|---|
| | Concentration of the active | Kill ratio (%) | |
| Test chemical | ingredient (ppm) | 2 days later | 7 days later |
| No. 1 + [A] | 40 + 20 | 100 | |
| | 20 + 10 | 20 | 85 |
| No. 1 + [B] | 40 + 4 | 100 | |
| | 20 + 2 | 40 | 75 |
| No. 2 + [A] | 40 + 20 | 100 | |
| | 20 + 10 | 20 | 80 |
| No. 2 + [B] | 40 + 4 | 100 | |
| | 20 + 2 | 30 | 75 |
| No. 3 + [A] | 40 + 20 | 100 | |
| | 20 + 10 | 40 | 100 |
| No. 3 + [B] | 40 + 4 | 100 | |
| | 20 + 2 | 45 | 80 |
| No. 4 + [A] | 40 + 20 | 100 | |
| | 20 + 10 | 35 | 95 |
| No. 4 + [B] | 40 + 4 | 100 | |
| | 20 + 2 | 50 | 90 |
| No. 5 + [A] | 40 + 20 | 100 | |
| | 20 + 10 | 50 | 100 |
| No. 5 + [B] | 40 + 4 | 100 | |
| | 20 + 2 | 70 | 100 |
| No. 1 | 40 | 35 | 35 |
| No. 2 | 40 | 30 | 30 |
| No. 3 | 40 | 40 | 40 |
| No. 4 | 40 | 40 | 45 |
| No. 5 | 40 | 55 | 60 |
| [A] | 20 | 0 | 35 |
| [B] | 4 | 0 | 40 |
| Non-treated | — | 0 | 0 |

Note
1. None of the mixed and single chemicals used in Example 3 showed phytotoxicity.
2. Compounds Nos. 1, 2, 3, 4 and 5 of general formula (I) used in this invention are the same compounds as in Example 1.
3. Compounds (according to group (2) insecticides mentioned above) used in this invention
[A]: diflubenzuron
[B]: N—(2,6-difluorobenzoyl)-N'[3,5-dichloro-4-(3-chloro-5-trifluoromethyl-2-pyridyloxy)phenyl]urea

EXAMPLE 4

Plutella test

Testing method

A water dilution of the active compounds in a predetermined concentration prepared as in Example 1 was sprayed onto cabbage seedlings before head formation, about 15 cm tall, planted in pots having a diameter of 9 cm in an amount of 20 ml per pot by means of spray gun. After the spray was air-dried, ten 4th instar larvae of organophosphorus-resistant diamondback moth (*Plutella maculipennis*) were inoculated in each pot. The pots were each placed in a constant temperature chamber. Two days later, the number of dead insects was counted, and the kill ratio was calculated. The above test was carried out through two replicates.

The results are shown in Table 4.

TABLE 4

| Test chemical | Plutella Test Concentration of the active ingredient (ppm) | Kill ratio (%) |
| --- | --- | --- |
| No. 1 + [A] | 40 + 40 | 100 |
| No. 2 + [A] | 40 + 40 | 100 |
| No. 3 + [A] | 40 + 40 | 100 |
| No. 4 + [A] | 40 + 40 | 100 |
| No. 5 + [A] | 40 + 40 | 100 |
| No. 1 | 40 | 25 |
| No. 2 | 40 | 20 |
| No. 3 | 40 | 35 |
| No. 4 | 40 | 35 |
| No. 5 | 40 | 40 |
| [A] | 40 | 30 |
| Non-treated | — | 0 |

Note
1. None of the mixed and single chemicals used in Example 4 showed phytotoxicity.
2. Compounds Nos. 1, 2, 3, 4 and 5 of the general formula (I) are the same as those used in Example 1.
3. Compound (according to group (2) insecticides mentioned above) used in this invention
[A]: 3-phenoxybenzyl 2-(4-ethoxyphenyl)-2-methyl-propylether

EXAMPLE 5

Wettable powder

Twenty parts of active substance of the formula (I), 20 parts of cartap, 55 parts of a 1:5 mixture of powdery diatomaceous earth and powdery clay, 2 parts of alkylbenzenesulfonate and 3 parts of sodium alkylnaphthalenesulfonate/formaldehyde condensate are pulverized and mixed to form a wettable powder.

(B) Biological Examples relating to novel substance combinations of (1) a nitromethylene derivative of formula (I) and a carboxylic acid ester compound of group (3) (formula II):

EXAMPLE 6

Plutella test

Preparation of a test chemical
Solvent: 3 parts by weight of xylol
Emulsifier: 1 part by weight of polyoxyethylene alkyl phenyl ether To prepare a formulation of active compounds, 1 part by weight of the active compouns were mixed with the aforesaid amount of the solvent containing the aforesaid amount of the emulsifier, and the mixture was diluted to a predetermined concentration with water.

Testing method

A water dilution of the active compounds in a predetermined concentration prepared as above was sprayed onto cabbage seedlings before head formation, about 15 cm tall, planted in pots having a diameter of 9 cm in an amount of 20 ml per pot by means of a spray gun. The spray was air-dried, and ten 4th instar larvae of organophosphorus resistant diamondback moth (Plutella maculipennis) were inoculated in each pot. The pots were placed in a constant temperature chamber, and the number of dead insects was counted 2 days later. The kill ratio was calculated. The test was carried out through two replicates.

The results are shown in Table 5.

TABLE 5

| Test chemical | Plutella test Concentration of the active ingredient (ppm) | Kill ratio (%) |
| --- | --- | --- |
| No. 1 + [B] | 40 + 8 | 100 |
| No. 1 + [E] | 40 + 8 | 90 |
| No. 1 + [G] | 40 + 80 | 90 |
| No. 2 + [A] | 40 + 8 | 100 |
| No. 2 + [C] | 40 + 8 | 95 |
| No. 2 + [F] | 40 + 8 | 90 |
| No. 3 + [B] | 40 + 8 | 100 |
| No. 3 + [C] | 40 + 8 | 100 |
| No. 3 + [G] | 40 + 80 | 100 |
| No. 4 + [A] | 40 + 8 | 100 |
| No. 4 + [D] | 40 + 8 | 90 |
| No. 4 + [E] | 40 + 8 | 100 |
| No. 5 + [D] | 40 + 8 | 100 |
| No. 5 + [E] | 40 + 8 | 100 |
| No. 5 + [F] | 40 + 8 | 100 |
| No. 1 | 40 | 25 |
| No. 2 | 40 | 20 |
| No. 3 | 40 | 35 |
| No. 4 | 40 | 35 |
| No. 5 | 40 | 40 |
| [A] | 8 | 30 |
| [B] | 8 | 30 |
| [C] | 8 | 20 |
| [D] | 8 | 5 |
| [E] | 8 | 20 |
| [F] | 8 | 15 |
| [G] | 80 | 25 |
| Non-treated | — | 0 |

Note
1. None of the mixed and single chemicals used in the test of Example 1 showed phytotoxicity.
2. Compounds of general formula (I) used in the invention:
Compound No. 1: 1-(2-methyl-5-pyridylmethyl)-2-(nitromethylene)tetrahydropyrimidine
Compound No. 2: 2-(2-methoxy-5-pyridylmethyl)-2-(nitromethylene)tetrahydropyrimidine
Compound No. 3: 1-(2-bromo-5-pyridylmethyl)-2-(nitromethylene)tetrahydropyrimidine
Compound No. 4: 1-(2-chloro-5-pyridylmethyl)-2-(nitromethylene)imidazolidine
Compound No. 5: 1-(2-fluoro-5-pyridylmethyl)-2-(nitromethylene)imidazolidine
3. Compounds (carboxylic acid esters of formula (II)
[A]: cyfluthrin
[B]: cyhalothrin
[C]: fenpropathrin
[D]: fenvalerate
[E]: flucythrinate
[F]: fluvalinate
[G]: α-cyano-5-phenoxybenzyl 1-p-ethoxyphenyl-2,2-2,2-dichlorocyclopropane-1-carboxylate

EXAMPLE 7

(emulsifiable concentrate)

Two parts of active substance of the formula (I), two parts of cyfluthrin, 81 parts of xylene, 8 parts by polyoxyethylene alkyl phenyl ether and 7 parts of calcium alkylbenzenesulfonate are mixed with stirring to form an emulsifiable concentrate.

(C) Biological Examples relating to novel substance combinations of (1) a nitromethylene derivative of formula (I) and a carbamate of group (4) (formula III):

EXAMPLE 8

Nilaparvata test

Preparation of a test chemical
Solvent: 3 parts by weight of xylol
Emulsifier: 1 part by weight of polyoxyethylene alkyl phenyl ether To prepare a formulation of active compounds, 1 part by weight of the active compounds were mixed with the aforesaid amount of the solvent containing the aforesaid amount of the emulsifier, and the mixture was diluted to a predetermined concentration with water.

Testing method

Three rice seedlings, 15 cm tall, were planted in each of pots having a diameter of about 13 cm. Ten days after the plantation, a water dilution of the active compounds in a predetermined concentration prepared as above was sprayed onto the plants in an amount of 20 ml per pot by means of a spray gun. After drying the spray, a cage was put over each pot, and ten 4th instar larvae of brown planthopper (*Nilaparvata lugens*) were inoculated in each pot. The pots were each placed in a constant temperature chamber. Three days later, the number of dead insects was counted, and the kill ratio was calculated. The above test was carried out through two replicates.

The results are shown in Table 6.

TABLE 6

| Test chemical | Nilaparvata test Concentration of the active components (ppm) | Kill ratio (%) |
|---|---|---|
| No. 1 + [A] | 8 + 100 | 95 |
| No. 1 + [H] | 8 + 100 | 80 |
| No. 2 + [D] | 8 + 100 | 80 |
| No. 2 + [I] | 8 + 100 | 85 |
| No. 2 + [B] | 8 + 100 | 100 |
| No. 3 + [C] | 8 + 100 | 90 |
| No. 3 + [D] | 8 + 100 | 90 |
| No. 4 + [A] | 8 + 100 | 100 |
| No. 4 + [B] | 8 + 100 | 100 |
| No. 4 + [F] | 8 + 100 | 100 |
| No. 5 + [B] | 8 + 100 | 100 |
| No. 5 + [E] | 8 + 100 | 90 |
| No. 5 + [G] | 8 + 100 | 80 |
| No. 1 | 8 | 10 |
| No. 2 | 8 | 5 |
| No. 3 | 8 | 15 |
| No. 4 | 8 | 30 |
| No. 5 | 8 | 35 |
| [A] | 100 | 50 |
| [B] | 100 | 45 |
| [C] | 100 | 10 |
| [D] | 100 | 15 |
| [E] | 100 | 20 |
| [F] | 100 | 50 |
| [G] | 100 | 5 |
| [H] | 100 | 15 |
| [I] | 100 | 35 |
| Non-treated | — | 0 |

Note
1. None of the mixed and single chemicals used in the tests of this example showed phytotoxicity.
2. Compounds of general formula (I) used in this invention:
Compound No. 1: 1-(2-methyl-5-pyridylmethyl)-2-(nitromethylene)-tetrahydropyrimidine
Compound No. 2: 1-(2-methoxy-5-pyridylmethyl)-2-(nitromethylene)-tetrahydroprimidine
Compound No. 3: 1-(2-bromo-5-pyridylmethyl)-2-(nitromethylene)-tetrahydropyrimidine
Compound No. 4: 1-(2-chloro-5-pyridylmethyl)-2-(nitromethylene)imidazolidine
Compound No. 5: 1-(2-fluoro-5-pyridylmethyl)-2-(nitromethylene)imidazolidine
3. Compounds (carbamates of formula III) used in this invention
[A]: propoxur
[B]: BPMC
[C]: isoprocarb
[D]: metolcarb
[E]: xylylcarb
[F]: carbofuran
[G]: carbosulfan
[H]: aminosulfan
[I]: bendiocarb

EXAMPLE 9

Aphis test

Testing method

Cotton aphids (*Aphis gossypii*) which were bred were inoculated in eggplants seedlings, about 15 cm tall, grown in pots having a diameter of 9 cm at a rate of about 100 per seedlings. One day after the inoculation, a water dilution in a predetermined concentration of the active compounds prepared as in Example 8 was sprayed by means of a spray gun at a rate of 20 ml per pot. After the spraying, the pots were left to stand in a greenhouse kept at 28° C. Two days after the spraying, the number of dead insects was counted, and the kill ratio was calculated.

The results are shown in Table 7.

TABLE 7

| Test chemical | Aphis Test Concentration of the active components (ppm) | Kill ratio (%) |
|---|---|---|
| No. 1 + [A] | 40 + 40 | 100 |
| No. 1 + [B] | 40 + 40 | 100 |
| No. 2 + [A] | 40 + 40 | 100 |
| No. 2 + [B] | 40 + 40 | 100 |
| No. 3 + [A] | 40 + 40 | 100 |
| No. 3 + [B] | 40 + 40 | 100 |
| No. 4 + [A] | 40 + 40 | 100 |
| No. 4 + [B] | 40 + 40 | 100 |
| No. 4 + [B] | 40 + 40 | 100 |
| No. 5 + [A] | 40 + 40 | 100 |
| No. 5 + [B] | 40 + 40 | 100 |
| No. 1 | 40 | 17 |
| No. 2 | 40 | 22 |
| No. 3 | 40 | 26 |
| No. 4 | 40 | 41 |
| No. 5 | 40 | 37 |
| [A] | 40 | 36 |
| [B] | 40 | 40 |
| Non-treated | — | 0 |

Note
1. None of the mixed and single chemicals used in the tests of this example showed phytotoxicity.
2. Compounds Nos. 1, 2, 3, 4 and 5 of general formula (I) used in this invention are the same as those used in Example 8.
3. Compounds (carbamates of formula III) used in the invention
[A]: ethiofencarb
[B]: pirimicarb

EXAMPLE 10

(wettable powder)

Twenty parts of active substance of the formula (I), 20 parts of propoxur, 55 parts of a 1:5 mixture of powdery diatomaceous earth and powdery clay, 2 parts of sodium alkylbenzenesulfonate and 3 parts of sodium alkylbenzenesulfonate and 3 parts of sodium alkylnaphthalene sulfonate/formaldehyde condensate are pulverized and mixed to form a wettable powder.

EXAMPLE 11

(dust)

One part of active substance of the formula (I), one part of BPMC and 98 parts of powdery clay are pulverized and mixed to form a dust.

EXAMPLE 12

(granules)

Ninety-six parts of clay mineral particles having a particle size distribution between 0.2 and 2 mm are put in a rotary mixer, and with rotation, 2 parts of active substance of formula (I) and 2 parts of carbofuran and sprayed onto the particles to wet them uniformly and the particles are dried to form granules.

(D) Biological Examples relating to novel substance combinations of (1) a nitromethylene derivative of formula (I) and an organophosphate ester of formula (IV):

EXAMPLE 13

Cnaphalocrocis test

Preparation of a test chemical

Solvent: 3 parts by weight of xylol
Emulsifier: 1 part by weight of polyoxyethylene alkyl phenyl ether To prepare a formulation of active compounds, 1 part by weight of the active compounds were mixed with the aforesaid amount of the solvent containing the aforesaid amount of the emulsifier, and the mixture was diluted to a predetermined concentration with water.

Testing method

Three rice seedlings, 15 cm tall, were planted in each of vinyl resin pots having a diameter of 9 cm. Ten days after the plantation, a water dilution of the active compounds in a predetermined concentration prepared as above was sprayed onto the plants in an amount of 20 ml per pot by means of a spray gun. After air drying the spray, a plastic net cylinder having a diameter of 9 cm and a height of 25 cm was put over each pot, and ten 4th instar larvae of paddy leaf roller (*Cnaphalocrocis medinalis*) were inoculated in each pot. The pots were placed in a constant temperature chamber. Two days later, the number of dead insects was counted, and the kill ratio was then calculated. The above test was carried out through two replicates.

The results are shown in Table 8.

TABLE 8

| Test chemical | Onaphalocrocis test Concentration of the active components (ppm) | Kill ratio (%) |
|---|---|---|
| No. 1 + [A] | 40 + 8 | 100 |
| No. 1 + [D] | 40 + 8 | 90 |
| No. 2 + [B] | 40 + 8 | 90 |
| No. 2 + [C] | 40 + 8 | 100 |
| No. 3 + [A] | 40 + 8 | 100 |
| No. 3 + [B] | 40 + 8 | 100 |
| No. 4 + [B] | 40 + 8 | 100 |
| No. 4 + [C] | 40 + 8 | 100 |
| No. 5 + [C] | 40 + 8 | 100 |
| No. 5 + [D] | 40 + 8 | 100 |
| No. 1 | 40 | 10 |
| No. 2 | 40 | 15 |
| No. 3 | 40 | 15 |
| No. 4 | 40 | 20 |
| No. 5 | 40 | 30 |
| [A] | 8 | 40 |
| [B] | 8 | 30 |
| [C] | 8 | 50 |
| [D] | 8 | 30 |
| Non-treated | — | 0 |

Note
1. None of the mixed and single chemicals used in the tests of this example showed phytotoxicity.
2. Compounds of general formula (I) used in this invention:
Compound No. 1: 1-(2-methyl-5-pyridylmethyl)-2-(nitromethylene)-tetrahydropyrimidine
Compound No. 2: 1-(2-methoxy-5-pyridylmethyl)-2-(nitromethylene)-tetrahydropyrimidine
Compound No. 3: 1-(2-bromo-5-pyridylmethyl)-2-(nitromethylene)-tetrahydropyrimidine
Compound No. 4: 1-(2-chloro-5-pyridylmethyl)-2-(nitromethylene)imidazolidine
Compound No. 5: 1-(2-fluoro-5-pyridylmethyl)-2-(nitromethylene)imidazolidine
3. Compounds (organophosphate esters of formula IV) used in this invention
[A]: isoxathin
[B]: pyridaphenthion
[C]: tetrachlorvinphos
[D]: sulprofos

EXAMPLE 14

Plutella test

Testing method

A water dilution of the active compounds in a predetermined concentration prepared as in Example 13 was sprayed onto cabbage seedlings before heading, about 15 cm tall and grown in pots having a diameter of 9 cm, at a rate of 20 ml per pot. After air-drying the sprayed chemical, ten 4th instar larvae of organophosphate-resistant diamondback (*Plutella maculipennis*) moth were inoculated per pot. The pots were placed in a constant-temperature chamber. Two days later, the number of dead insects was counted, and the kill ratio was calculated. The tst was conducted through two replicates.

The results are shown in Table 9.

TABLE 9

| Test chemical | Plutella test Concentration of the active components (ppm) | Kill ratio (%) |
|---|---|---|
| No. 1 + [A] | 40 + 40 | 100 |
| No. 1 + [B] | 40 + 40 | 100 |
| No. 1 + [D] | 40 + 40 | 100 |
| No. 2 + [A] | 40 + 40 | 100 |
| No. 2 + [B] | 40 + 40 | 100 |
| No. 2 + [C] | 40 + 40 | 100 |
| No. 3 + [A] | 40 + 40 | 100 |
| No. 3 + [B] | 40 + 40 | 100 |
| No. 3 + [C] | 40 + 40 | 100 |
| No. 4 + [B] | 40 + 40 | 100 |
| No. 4 + [C] | 40 + 40 | 100 |
| No. 4 + [D] | 40 + 40 | 100 |
| No. 5 + [A] | 40 + 40 | 100 |
| No. 5 + [C] | 40 + 40 | 100 |
| No. 5 + [D] | 40 + 40 | 100 |
| No. 1 | 40 | 25 |
| No. 2 | 40 | 20 |
| No. 3 | 40 | 35 |
| No. 4 | 40 | 35 |
| No. 5 | 40 | 40 |
| [A] | 40 | 25 |
| [B] | 40 | 40 |
| [C] | 40 | 30 |
| [D] | 40 | 30 |
| Non-treated | — | 0 |

Note
1. None of the mixed and single chemicals used in the test of Example 14 showed phytotoxicity.
2. Compounds Nos. 1, 2, 3, 4 and 5 of general formula (I) used in the invention are the same as those used in Example 13.
3. Compounds (organophosphate esters of formula IV) used in the invention
[A]: prothiofos
[B]: pirimiphos-methyl
[C]: chlorpyrifos
[D]: acephate

EXAMPLE 15

Myzus test

Testing method

Green peach aphids (*Myzus persicae*) having resistance to organophosphates and carbamates were inoculated in eggplant seedlings, about 20 cm tall and grown in pots having a diameter of cm, at a rate of about 100 per seedling. One day after the inoculation, a water dilution of the active compounds in a predetermined concentration prepared as in Example 13 was sprayed onto the plants at a rate of 20 ml per pot. After the spraying, the pots were left to stand in a greenhouse kept at 28° C. Three days after the spraying, the number of dead insects was counted, and the kill ratio was calculated.

The results are shown in Table 10.

TABLE 10

| | Myzus test | |
|---|---|---|
| Test chemical | Concentration of the active components (ppm) | Kill ratio (%) |
| No. 1 + [A] | 40 + 40 | 100 |
| No. 1 + [B] | 40 + 40 | 100 |
| No. 2 + [A] | 40 + 40 | 100 |
| No. 2 + [B] | 40 + 40 | 100 |
| No. 3 + [A] | 40 + 40 | 100 |
| No. 3 + [B] | 40 + 40 | 100 |
| No. 4 + [A] | 40 + 40 | 100 |
| No. 4 + [B] | 40 + 40 | 100 |
| No. 5 + [A] | 40 + 40 | 100 |
| No. 5 + [B] | 40 + 40 | 100 |
| No. 1 | 40 | 31 |
| No. 2 | 40 | 25 |
| No. 3 | 40 | 38 |
| No. 4 | 40 | 30 |
| No. 5 | 40 | 44 |
| [A] | 40 | 15 |
| [B] | 40 | 8 |
| Non-treated | — | 0 |

Note
1. None of the mixed and single chemicals used in the test of Example 3 showed phytotoxicity.
2. Compounds Nos. 1, 2, 3, 4 and 5 of general formula (I) used in this invention are the same as those used in Example 13.
3. Compounds (organophosphate esters of formula IV) used in the invention
[A]: disulfoton
[B]: vamidothion

EXAMPLE 16

(wettable powder)

Twenty parts of active substance of the formula (I), 20 parts of prothiofos, 55 parts of a 1:5 mixture of powdery diatomaceous earth and powdery clay, 2 parts of sodium alkylbenzenesulfonate and 3 parts of sodium alkylnaphthalenesulfonate/formaldehyde condensate are pulverized and mixed to form a wettable powder.

EXAMPLE 17

(dust)

One part of active substance of the formula (I), two parts of pyridaphenthion and 97 parts of powdery clay are pulverized and mixed to form a dust.

EXAMPLE 18

(granules)

Ninety-five parts of clay mineral particles having a particle size distribution between 0.2 and 2 mm are put in a rotary mixer, and with rotation, 2 parts of active substance of formula (I) and 3 parts of disulfoton are sprayed onto the particles to wet them uniformly and the particles are dried to form granules.

It is understood that the specification and examples are illustrative but not limitative of the present invention and that other embodiments within the spirit and scope of the invention will suggest themselves to those skilled in the art.

We claim:

1. An inseciticidal composition comprising an insecticidally effective amount of (1) a nitromethylene derivative of the formula

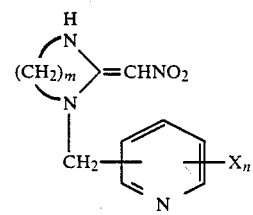

in which
X is a lower alkyl group, a lower alkoxy group or a halogen atom,
n is 0, 1 or 1, and
m is 2 or 3, and
(2) is chlorpyrifos methyl or chlorpyrifos, wherein the ratio of the nitromethylene derivative to chlorpyrifos methyl is 1:1 to 5:1 or wherein the ratio of the nitromethylene derivative to chlorpyrifos is 1:1.

2. A composition according to claim 1 wherein the second ingredient is chlorpyrifos methyl.

3. A method of combating insects which comprises applying to such insects or to an insect habitat an insecticidally effective amount of a composition according to claim 1.

* * * * *

UNITED STATES PATENT AND TRADEMARK OFFICE
CERTIFICATE OF CORRECTION

PATENT NO.   : 4,780,457
DATED        : Oct. 25, 1988
INVENTOR(S)  : Tsuboi et al.

It is certified that error appears in the above-identified patent and that said Letters Patent is hereby corrected as shown below:

| | |
|---|---|
| Col. 4, line 65 | Correct spelling of --tetrahydropyrimidine-- |
| Col. 11, line 45 | Delete "in general" in second instance |
| Col. 22, line 32 | Delete "1" in second instance and substitute --2-- |

Signed and Sealed this

Twenty-first Day of November, 1989

Attest:

JEFFREY M. SAMUELS

Attesting Officer    Acting Commissioner of Patents and Trademarks